(12) United States Patent
Draper et al.

(10) Patent No.: US 9,766,599 B2
(45) Date of Patent: Sep. 19, 2017

(54) DRUG DELIVERY DEVICE

(71) Applicant: Sanofi-Aventis Deutschland GmbH, Frankfurt am Main (DE)

(72) Inventors: Paul Richard Draper, Worcestershire (GB); Joseph Butler, Warwickshire (GB); Barry Yates, Warwickshire (GB); Stephen Francis Gilmore, Bristol (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/163,436

(22) Filed: Jan. 24, 2014

(65) Prior Publication Data

US 2014/0172162 A1    Jun. 19, 2014

Related U.S. Application Data

(62) Division of application No. 14/232,502, filed as application No. PCT/EP2012/063622 on Jul. 12, 2012.

(Continued)

(30) Foreign Application Priority Data

Jul. 15, 2011 (EP) .................................. 11174121

(51) Int. Cl.
*G06K 19/00* (2006.01)
*G05B 11/00* (2006.01)
(Continued)

(52) U.S. Cl.
CPC .............. *G05B 11/00* (2013.01); *A61M 5/24* (2013.01); *A61M 5/31551* (2013.01);
(Continued)

(58) Field of Classification Search
USPC ................ 235/375, 385, 435, 439, 454, 462
See application file for complete search history.

(56) References Cited

U.S. PATENT DOCUMENTS

| 2004/0056097 A1 | 3/2004 | Walmsley et al. |
| 2004/0083138 A1 | 4/2004 | Silverbrook et al. |

(Continued)

FOREIGN PATENT DOCUMENTS

| EP | 2428238 A1 | 3/2012 |
| WO | 02092153 A2 | 11/2002 |

(Continued)

OTHER PUBLICATIONS

European Search Report for EP Application No. 14153576, completed Aug. 6, 2014.

(Continued)

*Primary Examiner* — Matthew Mikels
(74) *Attorney, Agent, or Firm* — McDonnell Boehnen Hulbert & Berghoff LLP

(57) ABSTRACT

A drug delivery device comprising;
  a housing;
  a cylindrical member configured to be rotatably supported inside the housing, wherein the outer surface of the cylindrical member is provided with a track comprising a sequence of encoded images; and
  a sensor directed at the track of the cylindrical member and configured to detect features of the encoded images.

11 Claims, 16 Drawing Sheets

Related U.S. Application Data

(60) Provisional application No. 61/570,307, filed on Dec. 14, 2011.

(51) Int. Cl.
  *A61M 5/315* (2006.01)
  *A61M 5/24* (2006.01)
  *G07F 17/00* (2006.01)
  *G06M 1/272* (2006.01)
  *A61M 37/00* (2006.01)
  *A61M 5/31* (2006.01)
  *G06M 1/22* (2006.01)

(52) U.S. Cl.
  CPC .... *A61M 5/31556* (2013.01); *A61M 5/31568* (2013.01); *G06M 1/272* (2013.01); *G07F 17/0092* (2013.01); *A61M 5/3156* (2013.01); *A61M 5/31585* (2013.01); *A61M 37/00* (2013.01); *A61M 2005/3126* (2013.01); *A61M 2205/3306* (2013.01); *A61M 2205/50* (2013.01); *A61M 2205/8212* (2013.01); *G06M 1/22* (2013.01)

(56) References Cited

U.S. PATENT DOCUMENTS

| | | | |
|---|---|---|---|
| 2005/0001033 A1* | 1/2005 | Cheong | G06T 1/0021 235/454 |
| 2006/0224123 A1 | 10/2006 | Friedli et al. | |
| 2008/0000991 A1 | 1/2008 | Yin et al. | |
| 2008/0089552 A1* | 4/2008 | Nakamura | G06T 1/0085 382/100 |
| 2008/0287865 A1* | 11/2008 | Nielsen et al. | 604/65 |

FOREIGN PATENT DOCUMENTS

| | | |
|---|---|---|
| WO | 2006120182 A1 | 11/2006 |
| WO | 2010/052275 | 5/2010 |
| WO | 2010142598 A2 | 12/2010 |

OTHER PUBLICATIONS

EP Patent Application No. 11174121.1-2320 Communication dated Apr. 16, 2012.

* cited by examiner

Fig. 11

DRUG DELIVERY DEVICE

CROSS REFERENCE TO RELATED APPLICATIONS

The present application is a divisional application of U.S. patent application Ser. No. 14/232,502, filed Jan. 13, 2014 which is a 35 U.S.C. 371 National Application of PCT/EP2012/063622 filed Jul. 12, 2012, which claims priority to European Patent Application No. 11174121.1 filed Jul. 15, 2011 and U.S. Provisional Patent Application No. 61/570,307, filed Dec. 14, 2011 the entire contents of which are incorporated entirely herein by reference.

FIELD

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

A first aspect of the invention provides a drug delivery device comprising;
  a housing;
  a cylindrical member configured to be rotatably supported inside the housing, wherein the outer surface of the cylindrical member is provided with a track comprising a sequence of encoded images; and
  a sensor directed at the track of the cylindrical member and configured to detect features of the encoded images.

The track may be a helical track and the housing and the cylindrical member may be configured such that the cylindrical member moves in a first axial direction relative to the housing when rotated in a first rotational direction relative to the housing.

The cylindrical member may be configured to be rotated from an initial position into a number of discrete rotational positions, wherein each successive rotational position is represented by the next in the sequence of encoded images. The encoded images may be optically encoded images and the sensor may be an optical sensor configured to detect light intensity values at multiple locations on each encoded image. The housing may also support a light source configured to illuminate the track.

The encoded image may be an optically encoded image that is a representation of a value. The value could correspond to a position of a cylindrical member. The cylindrical member could be operationally coupled to a dose setting and/or dispensing mechanism. The position of the cylindrical member could correspond to a dialled dose size.

The sensor detecting the image may be connected to a processor that determines the corresponding value. Having a certain value encoded into an optical image could allow for absolute value determination.

The successive rotational position of the cylindrical member may be represented by the next in the sequence of encoded images. The images in the sequence may be separated, e.g. the images may be separated by a white separation space. This may support identification of the individual image.

An image could be as complex as a figurative landscape or portrait image. Having images of, e.g., 81 different faces could be used to represent 81 different values. Hence, each image has encoded a certain value.

An image, however, may be less complex, and represent a rather abstract pattern. Again, e.g., 81 different images could be used to represent 81 different values. It is immediately understood that the number of values is almost arbitrary. The determination of a value corresponding to an encoded image is merely dependent upon the capabilities of the sensor.

The encoding may comprise light intensities. The light intensities could comprise black and white values, grey levels, or colors.

The light intensity could be an integral value of the area of the image. A sensor could determine the grey level of the entire area of image which corresponds to a certain value that is encoded in the image. For example, a sensor capable of determining 256 different grey levels could be used to determine 256 absolute position values that are encoded in 256 different images.

Alternatively, the light intensity could vary at multiple locations within the area of the image.

The light intensity variation at multiple locations could be encoded in terms of patterns. A pattern could comprise the whole area of the image. A pattern could comprise a partial area of the image. The image area could be segmented, e.g. into seven partial areas. Each partial area could be either black or white. Together, the encoded image would represent a 7-bit code system. However, any number of segments or partial areas may be used to make up an image that represents a code system with the respective number of bits.

The light intensity variation at multiple locations could be encoded in terms of a matrix. The matrix could be a dot matrix.

The device may further comprise a processor configured to receive electrical signals from the sensor and to identify an encoded image from the received signals. The processor may be configured to interpret the signals and to compare the interpreted signals to a stored record of encoded images. Each encoded image may comprise a plurality of adjacent identical code sections and the sensor may be configured to detect portions of two or more of the adjacent identical code sections.

The processor may be configured to receive image data from the sensor and to detect a geometric feature of the image data. The processor may be configured to detect encoded information from a location of the image that is in a predefined position relative to the geometric feature. The processor may be configured to detect encoded information from plural locations of the image that are in different predefined positions relative to the geometric feature. Each predefined position relative to the geometric feature may be defined by a pixel map comprising an arrangement of data bits.

The geometric feature may be a cross shaped feature of the image. The cross shaped feature may separate four adjacent identical code sections. Each of the identical code sections may comprise an arrangement of data bits. The processor may be configured to compare the received image data to the pixel map comprising an arrangement of data bits.

Each encoded image may be disposed within a boundary of a geometric feature. The processor may be configured to compare the received image data to the pixel map comprising an arrangement of data bits and to determine which of the pixels represents the centre of the predetermined geometric feature. The predetermined geometric feature may be a circular band.

Each data bit may be comprised of a plurality of pixels and each pixel of the pixel map may have an associated weighting value determined by its position within its respective data bit.

The device may further comprise a user actuatable plunger configured to cause expulsion of a drug from the drug delivery device and a switch, wherein depression of the plunger may be configured to cause the switch to switch from a first position to a second position. The device may further comprise a display and the processor may control the operation of the display.

The processor may be configured to determine a discrete rotational position of the member using the reconstructed encoded image, to determine a selected drug dose using the discrete rotational position of the member and to cause the selected drug dose to be displayed on the display.

The outer surface of the cylindrical member may be further provided with a detectable surface texture. The sensor may be an optical sensor and may be further configured to detect changes in light intensity values at the location of the surface texture when the cylindrical member rotates.

The device may further comprise a lens disposed in a line of sight of the sensor.

BRIEF DESCRIPTION OF THE DRAWINGS

Embodiments will now be described, by way of example only, with reference to the accompanying drawings, in which:

FIG. 9b shows a rearrangement of the image of FIG. 9a;

FIG. 11 is a table illustrating an encoding method which maximizes the number of white bits in an encoded image;

DETAILED DESCRIPTION OF PREFERRED EMBODIMENTS

Figure 1:
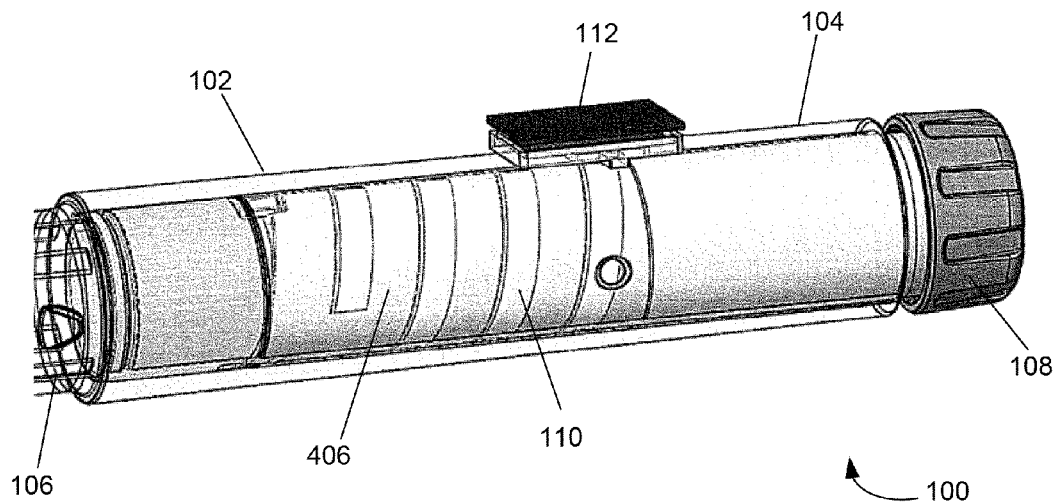
FIG. 1 shows a wireframe illustration of a drug delivery device suitable for implementing the present invention.

Referring firstly to FIG. 1, a wireframe illustration of a portion of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106, only a portion of which can be seen at the far left side of FIG. 1. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion. The threaded portion may have a smaller diameter than the remainder of the second housing part 106

A sensor 112 is supported on the first housing part 104. The sensor 112 may be received in a recess or window in the first housing part 104. The sensor 112 may comprise an add-on module, as shown. In some other embodiments, the sensor 112 may be integral with the housing 102. In some embodiments, the sensor 112 is an optical sensor. Optical sensors of the type manufactured by Avago Technologies may be suitable for use in the present invention. The first housing part 104 may also support a display (not shown in FIG. 1 but shown as 210 in FIG. 2). The display 210 may be an LCD display, a segmented display or any other suitable type of display. The display 210 may be located above the sensor 112. A number of electronic components, described in greater detail with reference to FIG. 2, may be supported in the recess or window.

An encoded member 406 is rotatably mounted inside the first housing part 104. The encoded member 406 is preferably a hollow cylinder and comprises, on its outer surface, a helical track 110. This helical track 110 comprises encoded information which is detectable by the sensor 112. The encoded member may be coupled to and configured to rotate with the rotatable dial 108.

The first housing part 104 contains a drug dose setting and delivery mechanism (not shown). The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way as the drug cartridge is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. This process is known as "dialling" a dose. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a button (not shown) which must be depressed in order to deliver the set drug dose. The display 210 may be configured to display information on the drug dose which has been set and/or delivered. The display 210 may further show additional information, such as the actual time, the time of the last usage/injection, a remaining battery capacity, one or more warning signs, and/or the like.

Figure 2:
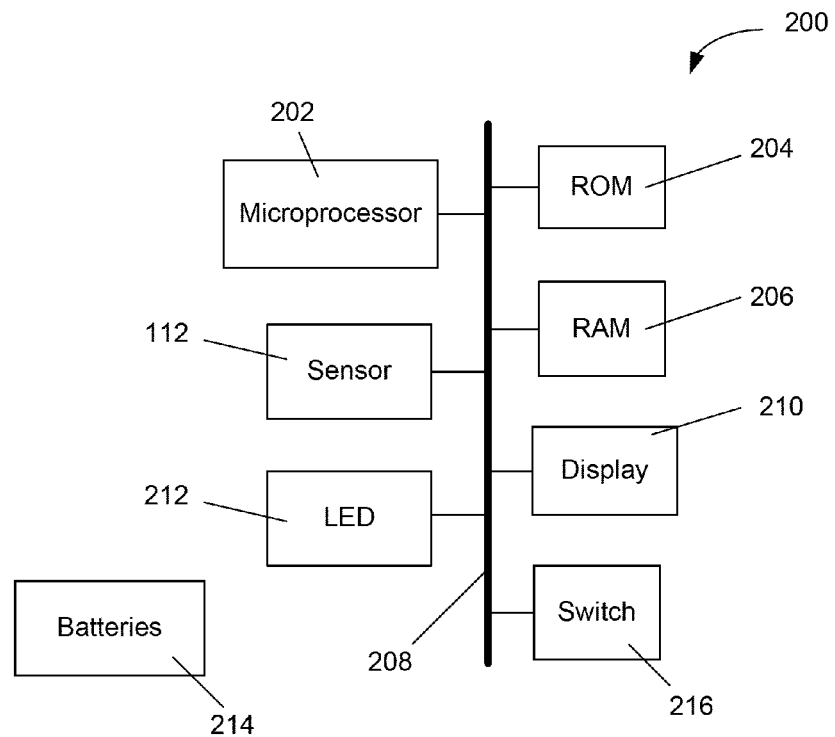
FIG. 2 shows a schematic diagram of some of the electronic components present in the drug delivery device of FIG. 1.

Referring now to FIG. 2, a schematic diagram of electrical circuitry 200 forming part of the drug delivery device 100 is shown. The circuitry 200 comprises a microprocessor 202, a non-volatile memory such as a ROM 204, a volatile memory such as a RAM 206, a display 210, the sensor 112, one or more LEDs 212, a switch 216 and a bus 208 connecting each of these components. The circuitry 200 also comprises batteries 214 or some other suitable source of power for providing power to each of the components. It will be apparent to the skilled person that other light sources, to replace the LED 212, may be suitable, for example incandescent bulbs etc.

The ROM 204 may be configured to store software and/or firmware. This software/firmware may control operations of the microprocessor 202. The microprocessor 202 utilises RAM 206 to execute the software/firmware stored in the ROM to control operation of the display 210. As such the microprocessor 202 may also comprise a display driver.

The microprocessor 202 is configured to receive signals from the sensor 112 and is configured to interpret these signals. Information is provided on the display 210 at suitable times by operation of the software/firmware and the microprocessor 202. This information may include measurements determined from the signals received by the microprocessor 202 from the sensor 112. For example, the sensor 112 may be an optical sensor configured to capture pixelated greyscale images of the encoded information. The captured image data is then sent to the microprocessor 202.

The one or more LEDs 212 are directed at the encoded member 406 in order to illuminate the encoded information of the helical track 110. This allows the sensor 112 to detect the encoded information. For example, the sensor 112 may detect the intensity pattern of light reflected from the helical track 110. The LED 212 and sensor 112 may be configured to operate at various wavelengths of light. The LED 212 and sensor 112 may, for example, operate in infra-red. The LED 212 and sensor 112 may be an integrated unit or may comprise separate units.

Figure 3:
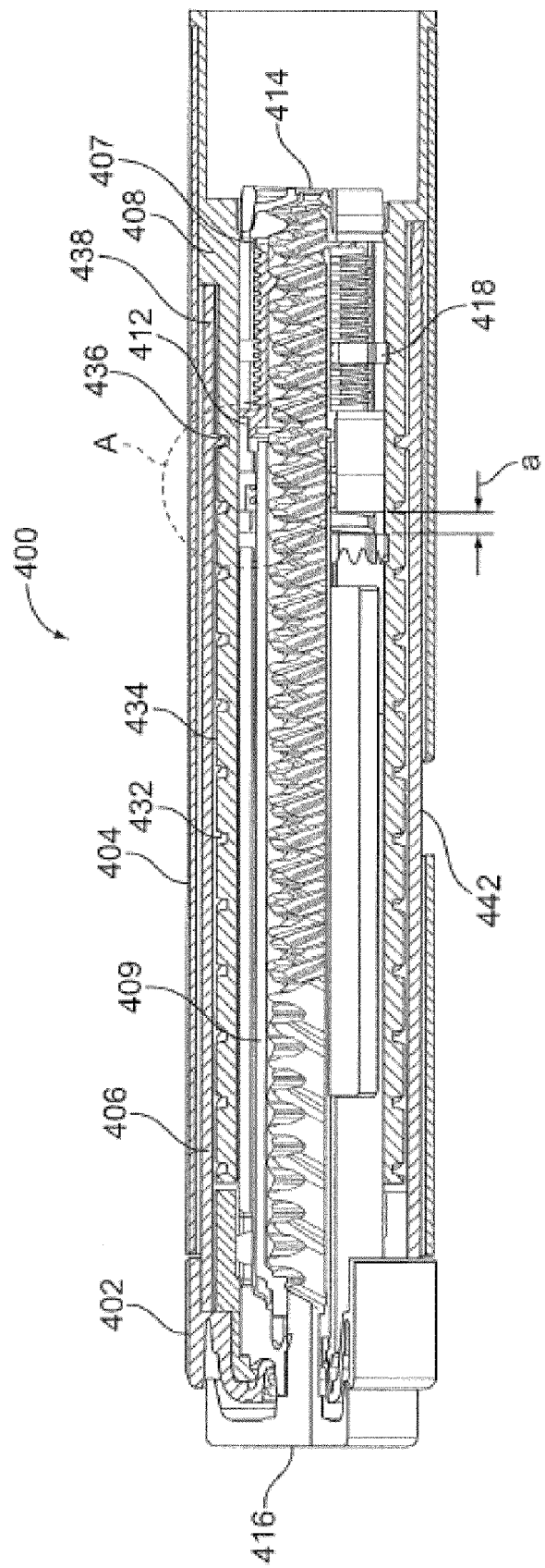
FIG. 3 shows a dose setting mechanism of a drug delivery device suitable for use with the invention.
Figure 4:
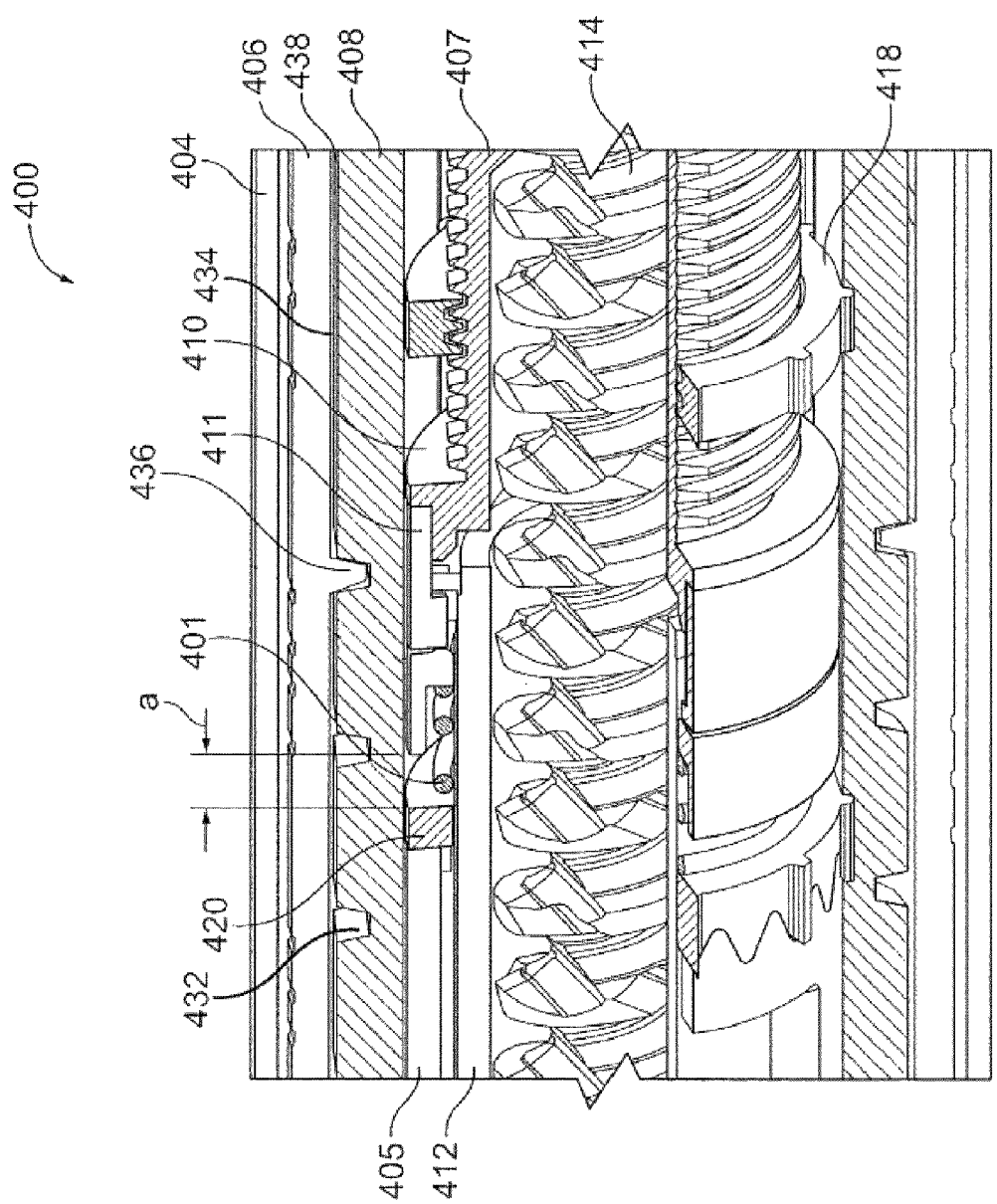
FIG. 4 shows detail of the dose setting mechanism of FIG. 3.
Figure 5:
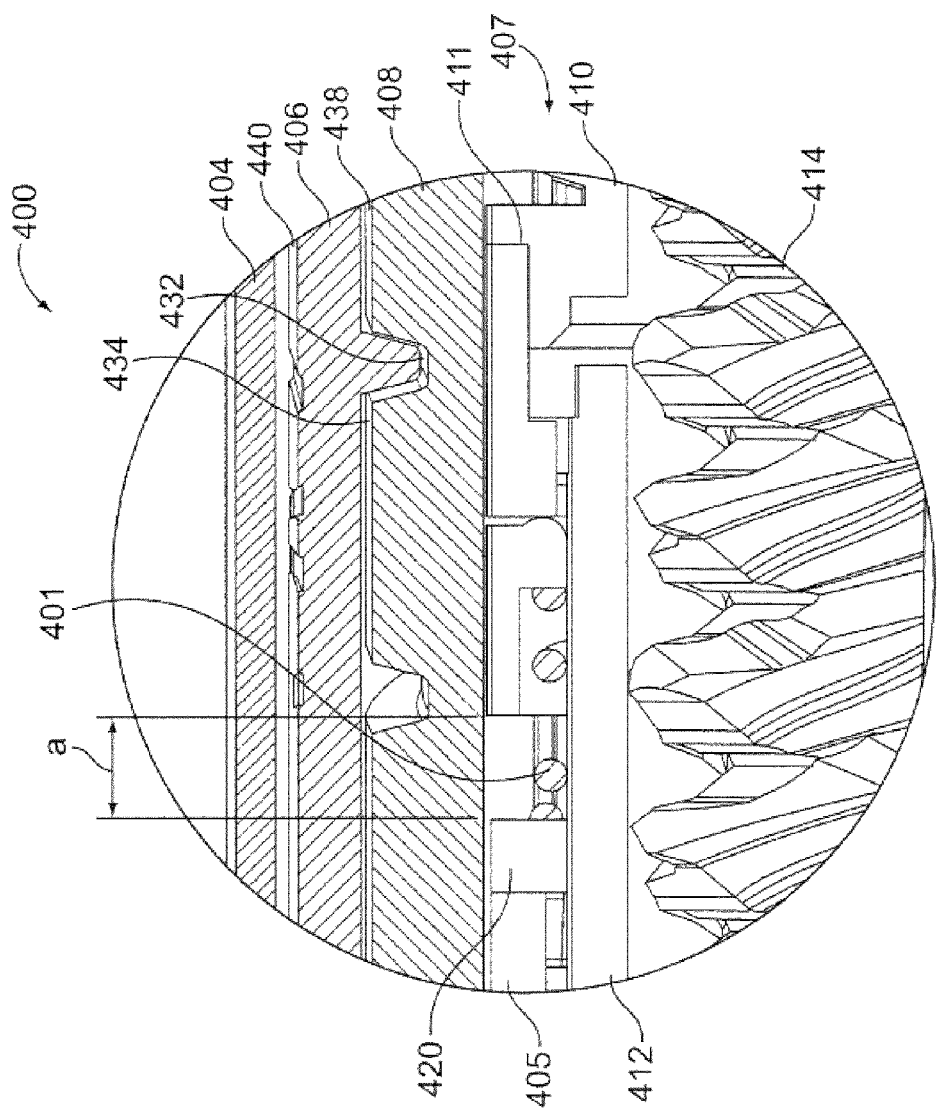
FIG. 5 shows a close up of the region marked 'A' in FIG. 3.

A fuller explanation of the operation of the dose setting and delivery mechanism supported within the second housing part 106 will now be given with reference to FIGS. 3 to 6. FIG. 3 is a cross-sectional view of a dose setting mechanism 400 of a drug delivery device. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and the encoded member 406. These components are preferably hollow cylinders arranged concentrically. The encoded member 406 is disposed between the outer and inner housings. The inner housing 408 comprises a groove 432 provided along an external surface 434 of the inner housing 408. A groove guide 436 provided on an inner surface 438 of the encoded member 406 is rotatably engaged with this groove 432. The encoded member 406 has information encoded on its outer surface 440 as will be described in more detail below with reference to FIG. 7.

A dose dial grip 402 is located at a proximal end of the outer housing 404. The dose dial grip 402 is disposed about an outer surface of a proximal end of the encoded member 406. An outer diameter of the dose dial grip 402 preferably corresponds to the outer diameter of the outer housing 404. The dose dial grip 402 is secured to the encoded member 406 to prevent relative movement between these two components. The dose dial grip 402 is represented in the external view of FIG. 1 by the rotatable dial 108. The dose dial grip 402 supports a dose button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that preferably extend over at least a majority of a length of the spindle. Each groove form is effectively continuous over a number of turns. In one preferred arrangement, each groove of the spindle 414 engages either a non-continuous helical groove form on a body portion or on a driver. Preferably, either or both a non-continuous thread form on a body and a driver consists of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. In one arrangement, the first driver portion 407 comprises a first component part 410 and a second component part 411. Alternatively, the first driver portion 407 is an integral component part.

With the dose setting mechanism 400, as a user dials a dose with the dose dial grip 402, the metal spring 401 is selected to be strong enough to maintain engagement of both clutched couplings: the clutched coupling between the clutch 405 and the encoded member 406 and clutched coupling between the first driver portion 407 and second driver portion 412. The encoded member 406 is coupled to the dose dial grip 402 such that when a user rotates the dose dial grip 402, the encoded member 406 also rotates. As the encoded member 406 is rotated in a first rotational direction, it moves axially in a proximal direction due to its threaded connection to the inner housing 408.

When the drug delivery device is being dispensed, the user applies an axial load to the dose button 416 located at the proximal end of the mechanism 400. The dose button 416 is axially coupled to the clutch 405 and this prevents relative axial movement. Therefore, the clutch 405 moves axially towards the cartridge end or the distal end of the dose setting mechanism 400. This movement disengages the clutch 405 from the encoded member 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. In one preferred arrangement, the outer surface of the dose limiter 418 and an internal surface of the inner housing 408 are keyed together by way of splines. This prevents relative rotation between the dose limiter 418 and the housing 408 while allowing relative longitudinal movement between these two components.

Figure 6:
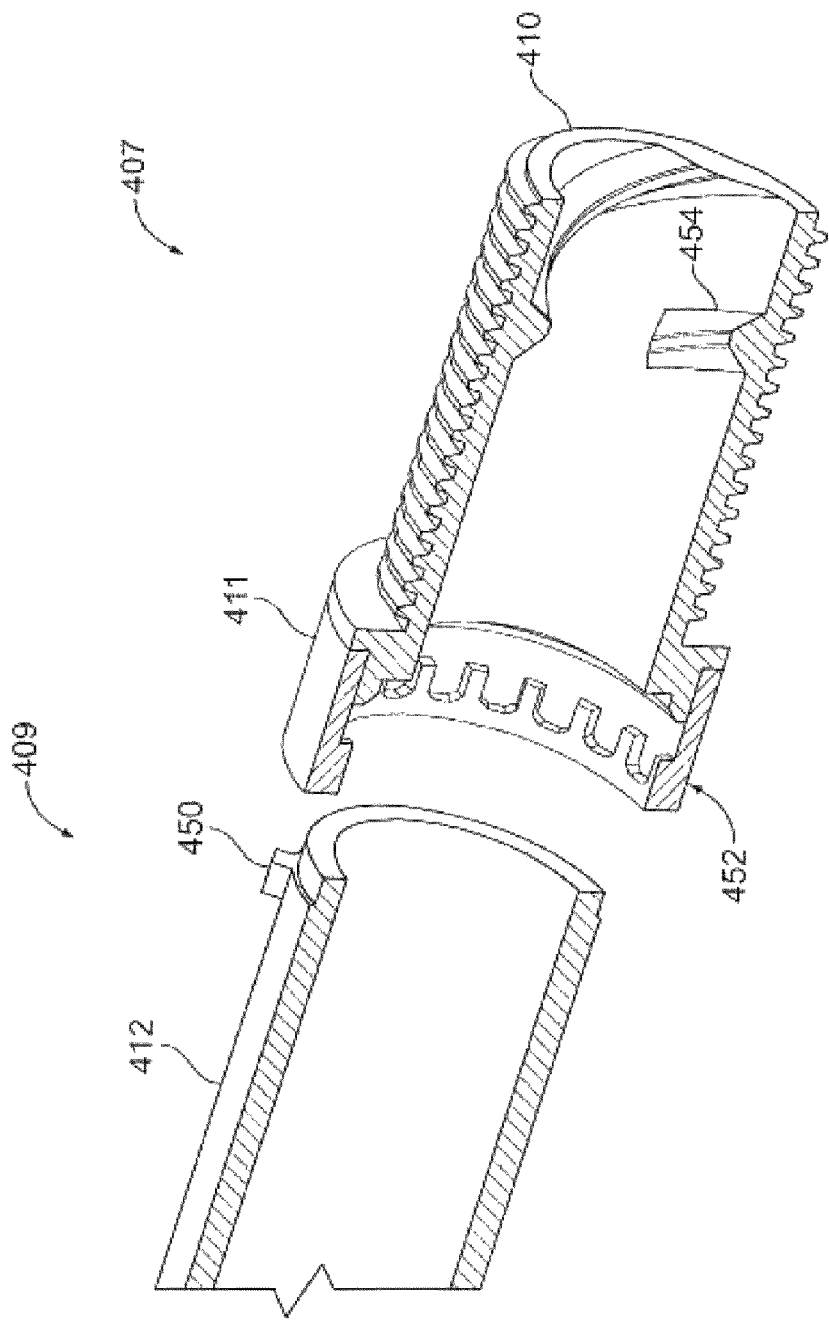
FIG. 6 is an exploded view showing details of a driver forming part of the dose setting mechanism of FIGS. 3 to 5.
Figure 10:
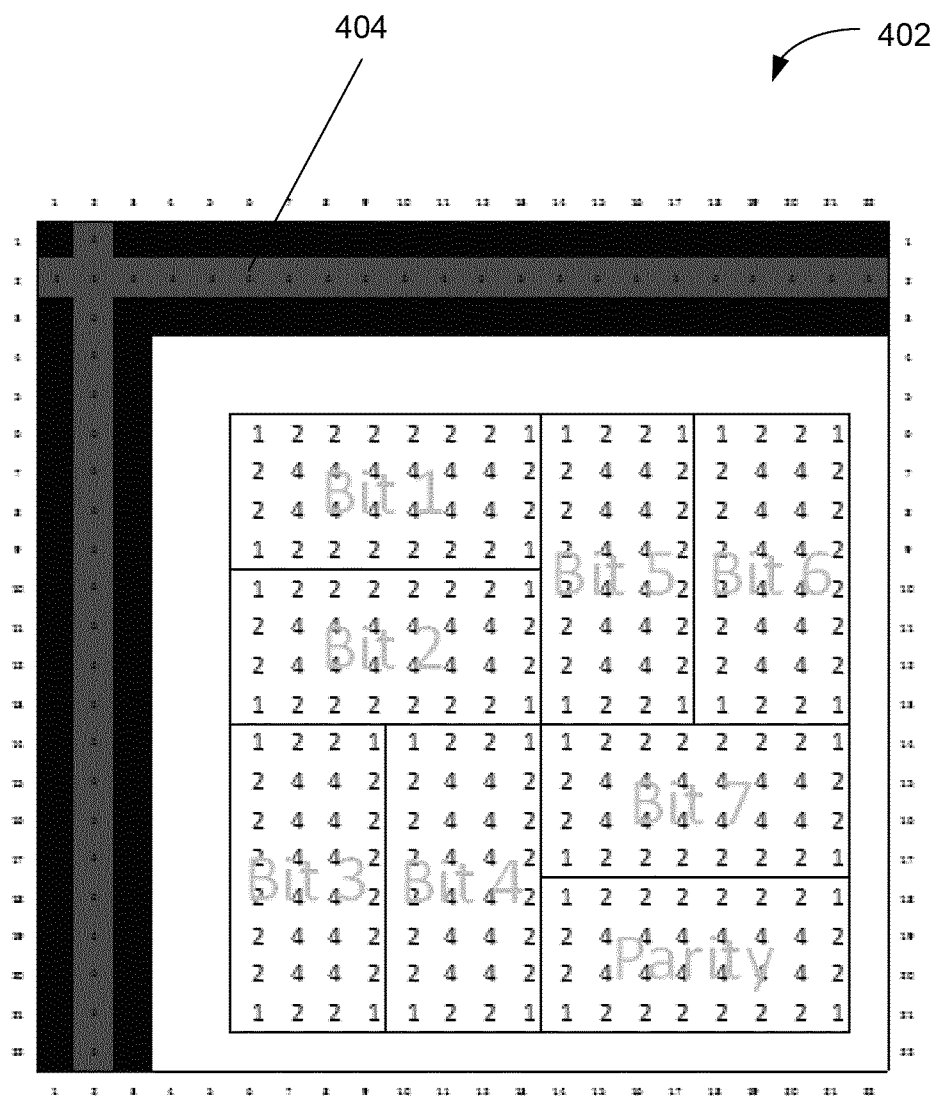
FIG. 10 shows the position of pixels and data bits in a pixel map.

FIG. 6 shows in detail a first arrangement of the first driver portion 407 and the second driver portion 412 illustrated in FIGS. 3 to 5. As illustrated in FIG. 10, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove rather than a complete helical groove. One advantage of this arrangement is that it is generally easier to manufacture.

One advantage of this dose setting mechanism 400 utilizing the inner housing 408 is that the inner housing 408 can be made from an engineering plastic that minimizes friction relative to the encoded member 406 groove guide 436 and the groove 432. For example, one such an engineering plastic could comprise Acetal. However, those skilled in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The groove guide 436 on the inner surface 438 of the member 406 may extend over a single turn or over a partial turn. Alternatively, this groove guide 436 may comprise several turns. The member 406 may be made of a plastic material. The inclusion of an inner housing 408 enables the encoded member 406 to have a helical thread or groove guide 436 on the inner surface 438 rather then the outer surface 440. This results in a number of advantages. For example, this results in the advantage of providing more surface area along the outer surface 440 of the encoded member 406 for the helical track 110. Another advantage is that this inner groove 436 is now protected from dirt ingress. In other words, it is more difficult for dirt to become logged in this inner groove interface than if the groove were provided along the outer surface 440 of the encoded member 406. This feature is particularly important for a re-useable drug delivery device which is required to function over a much longer period of time compared to a non re-useable device.

The effective driving diameter (represented by 'D') of the grooved interface between the encoded member 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member will rotate or lock to the inner body wherein this helix angle is proportional to the ratio of P/D.

A window 442 in the outer housing 404 of the drug delivery device 100 can be seen in FIG. 3. This window 442 may be configured to receive an insert (not shown), comprising the microprocessor 202, ROM 204, RAM 206, display electronics, sensor 112, LED 212, switch 216 and batteries 214 previously described. The sensor and LED 212 may be supported on a lowermost surface of the insert, so as to have direct access to the encoded member 406. The display 210 (not shown) may be disposed on top of the insert or may be integral with the insert. The display 210 may be larger than the window 442 and may therefore protrude from the outer housing 404. Alternatively, the display 210 may be configured to be received by the window 442 such that the display 210 is flush with the outer surface of the outer housing 404.

The dose setting mechanism 400 illustrated in FIG. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is de-coupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually de-couple the first driver portion 407 and second driver portion 412.

This axial movement of the first driver portion 407 towards the second driver portion 412 results in certain advantages. For example, one advantage is that the metal spring 401 will compress and will therefore close the Gap 'a' illustrated in FIGS. 3-5. This in turn prevents the clutch 405 from disengaging from the clicker 420 or from the encoded member 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the encoded member 406. As a consequence, the encoded member 406 cannot rotate relative to the inner housing 404. If the encoded member 406 is prevented from rotating then, as the spindle 414 is retracted back into the dose setting mechanism 400 and thereby re-set, there will be no risk of the encoded member 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver portion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

The dose setting mechanism described above is merely one example of a mechanism suitable for supporting the encoded member 406 and for implementing the present invention. It will be apparent to the skilled person that other mechanisms may also be suitable. For example, a mechanism which does not include an inner housing 408, but in which the encoded member 406 is still visible to the sensor 112 would be equally suitable.

The outer surface 440 of the encoded member 406 comprises a helical track 110, which is visible only in FIG. 1. This track 110 comprises a series of encoded images, which may be equally spaced and equally sized. Each of these images may be a matrix of points within a grid or a bar code. The code may be printed, marked, indented, etched or similar onto the helical track 110. The sensor 112 is configured to capture these images and to relay signals to the microprocessor 202. The microprocessor 202 is configured to employ software stored in the ROM 204 to determine the content of each image, for example the positions of the matrix which have dots, and to identify a corresponding rotational position of the encoded member 406 relative to the sensor 112. The microprocessor 202 may achieve this by consulting a table stored in the ROM 204 which relates the content of each image to a rotational position of the encoded member 406 and hence to a drug dose which has been dialled or delivered. This result may be stored to the ROM 204 of the device 100 and/or displayed on the display 210.

The pitch of the helical track 100 is the same as the pitch of the groove guide 436 of the encoded member 406 which engages with the inner housing groove 432. Therefore, when the encoded member 406 rotates and moves axially within the housing 102, the helical track 100 is always positioned underneath the sensor 112.

A typical field of view for an optical sensor 112 suitable for use in the present invention is 1 $mm^2$. Alignment of the encoded images of the track 110 with such a field of view can be difficult. In some embodiments, a lens (not shown) may be incorporated into the sensor 112 to increase the field of view without an unacceptable deterioration in sensitivity. This may ensure that each encoded image relating to a discrete rotational position of the encoded member 406 is legible.

Figure 7:
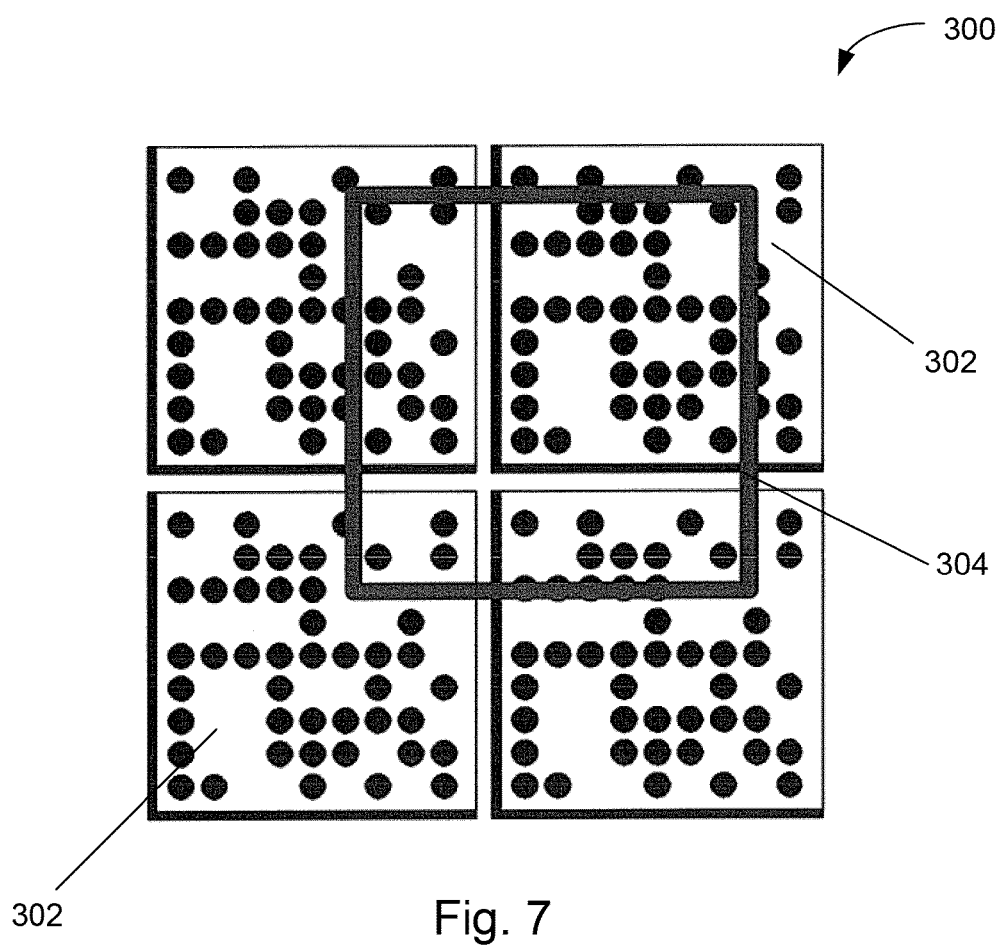
FIG. 7 shows an exemplary code section from an encoded member according to an embodiment of the invention.

In some embodiments, each of the encoded images comprises a repeated code pattern. An exemplary encoded image 300 representing a single rotational position is shown in FIG. 7. The encoded image 300 has a number of identical code patterns 302. In this instance four point-matrix code patterns 302 are arranged into a larger grid. The square 304 represents the field of view of the sensor 112. The repeated code patterns 302 mean that sensor position does not need to be as accurate as when only a single code pattern 302 is used. This allows for positional variability of the sensor 112 due to tolerance build up. Tolerance may be more likely to build up in one direction than another. For example, it may be found that the vertical alignment of the sensor 112 with the track 110 remains accurate but that variability in the circumferential alignment is seen. In this case only two repeated code patterns 302 may be used, arranged adjacent to one another along the length of the track 110.

The microprocessor 202 is programmed to recognise the edges of each of the code patterns 302 and to determine the full code based upon partial views of two or more identical code patterns 302. For example, where the encoded image 300 is a point-matrix code as shown in FIG. 7, and the sensor 112 is an optical sensor, the data output by the sensor 112 may comprise an array of light intensity values. The microprocessor 202 may use these light intensity values to identify the rows and columns of the matrix. The microprocessor 202 also determines whether each point in the matrix is black or white. The microprocessor 202 may then compare the data with a stored table relating the matrix pattern to a rotational position of the member 406. Where the encoded image 300 consists of a plurality of identical code patterns 302, the microprocessor 202 may identify the edges of each code pattern 302 in any known way. The microprocessor 202 may also then identify the rows and columns of any partial view of the code patterns 302 and may use this identification to virtually reconstruct one complete code pattern.

Where the device 100 is an insulin pen, a user of the device 100 may commonly need to administer between 1 and 80 International Units of insulin. Therefore, the helical track 110 preferably has at least 81 (including a zero position) discrete rotational positions, each represented by a unique encoded image 300. Where the encoded images are point-matrices, each of the 81 encoded images may be substantially different, i.e. there may be several differences between any two matrices. This allows for mistakes to be made by the microprocessor 202 in identifying the layout of the matrix while still allowing the microprocessor 202 to identify which rotational position the matrix encodes.

Figure 8:
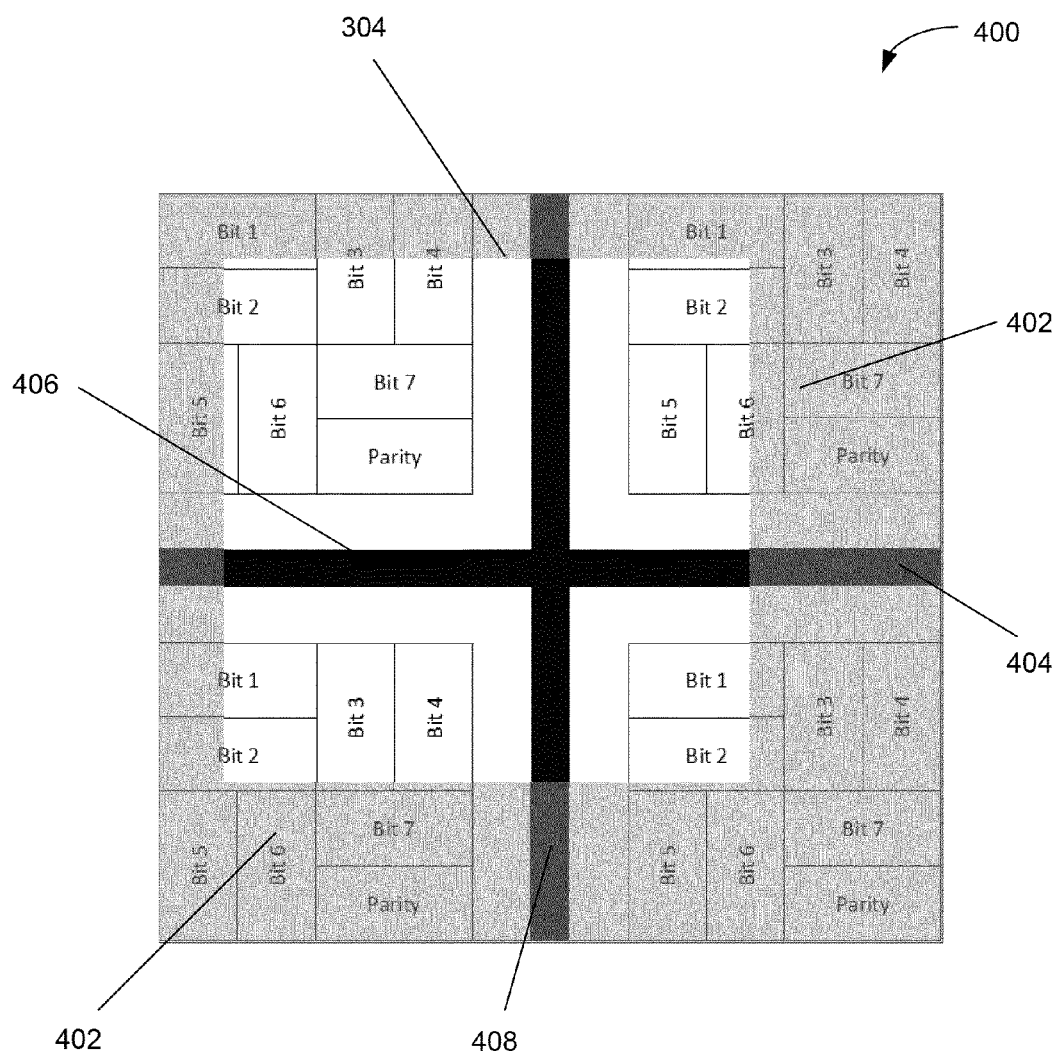
FIG. 8 shows a template for creating an encoded image according to an embodiment of the invention.

Further embodiments of encoded images suitable for use in the present invention will now be described with reference to FIGS. 8 to 12. FIG. 8 shows a template 400 for creating an encoded image consisting of four identical pixel maps 402 arranged into a larger grid. Each pixel map 402 may be comprised of a 22×22 pixel array. Each pixel map 402 comprises seven information bits (numbered 1 to 7) and one parity bit. When an encoded image 300 is created, each of the bits may be filled in black or left white.

The square 304 represents the field of view of the sensor 112. The sensor 112 captures an image of the portion of an encoded image which appears within its field of view. The field of view of the sensor 112 is larger than the repeated pixel maps 402 and so captures different portions of each of the pixel maps 402. The image captured by the sensor 112 is then analysed by the microprocessor 202 in order to reconstruct a single pixel map 402 from the portions of each of the pixel maps 402 present in the image. The position of the pixel maps 402 relative to the field of view of the sensor 112 is determined by detection of a datum feature. A datum feature is a geometric feature or shape which is distinct from any features of the pixel maps 402. Once the position of the pattern within the field of view is determined, the true encoded pattern can be virtually generated by manipulation of the pixel data from the captured image.

In the embodiment shown in FIGS. 8 to 12 the geometric feature (or datum feature) is a black cross 404 consisting of a horizontal band 406 and a vertical band 408, surrounded by a white border. The term "cross" as used herein may refer to a shape comprising two straight arms which intersect, preferably at right angles. Preferably the intersection occurs at a mid point of each of the two arms. The length and width of the bands 406, 408 is distinctly different from any pattern produced by possible combinations of black and white bits within the pixel maps 402.

The sensor 112 captures a pixelated image in grayscale, with high intensity pixels representing white areas and low intensity pixels representing black areas of the pattern. The microprocessor 202 is configured to implement an algorithm to detect the cross feature within the image. The algorithm detects the strongest horizontal and vertical lines, of a predetermined width, within the captured image. A line is assumed to be a band (horizontal or vertical) of low intensity pixels, surrounded by high intensity pixels. In order to accurately perform this detection, the arms of the cross and the pixels of the sensor 112 should have substantially the same orientation. In other words, a nominal 'horizontal' arm of the cross should preferably have the same orientation as a row of pixels, however the alignment does not need to be exact for the detection to be successful.

The cross detection algorithm for the horizontal band 406 may be described mathematically as follows, where 'n' refers to a pixel row number.

Calculate the sum of the intensity values for the pixels within each row:

$$\Sigma Row_n = Pixel_{n,1} + Pixel_{n,2} + Pixel_{n,3} + Pixel_{n,4} \ldots$$

Calculate the sum of row intensities over a range of rows. The size of the range should match the pixel width of the horizontal band 406 of the cross 404. In this example a 3 pixel band is used:

$$Band\_Sum\_Row_n = \Sigma Row_{n-1} + \Sigma Row_n + \Sigma Row_{n+1}$$

Calculate the compound intensity gradient of the band intensities.

$$Compound\_Gradient\_Row_n = (Band\_Sum\_Row_n - Band\_Sum\_Row_{n-1}) + (Band\_Sum\_Row_n - Band\_Sum\_Row_{n+1})$$

Any row with a positive compound gradient indicates a light band compared to its surroundings. Any row with a negative compound gradient indicates a dark band compared to its surroundings. The greater the magnitude of the compound gradient, the higher the intensity change between the band and its surrounding. Therefore the strongest horizontal black band within the image is identified by the highest magnitude negative compound gradient. Thresholds can be included to ensure that the strongest band is of sufficient intensity, and that it is a distinct solution from the next strongest band.

The same algorithm is then applied to the columns of the image to detect the strongest vertical black band. By initially combining the intensity of each pixel into a summation of the intensity for each row and column, the number of calculations required to solve the algorithm is significantly reduced when compared to continuing to consider, and conduct calculations on, each pixel individually. This results in a reduction in power consumption of the microprocessor 202 as well as an increase in the speed with which a determination of the rotational position of the encoded member 406 can be made.

Figure 9B:
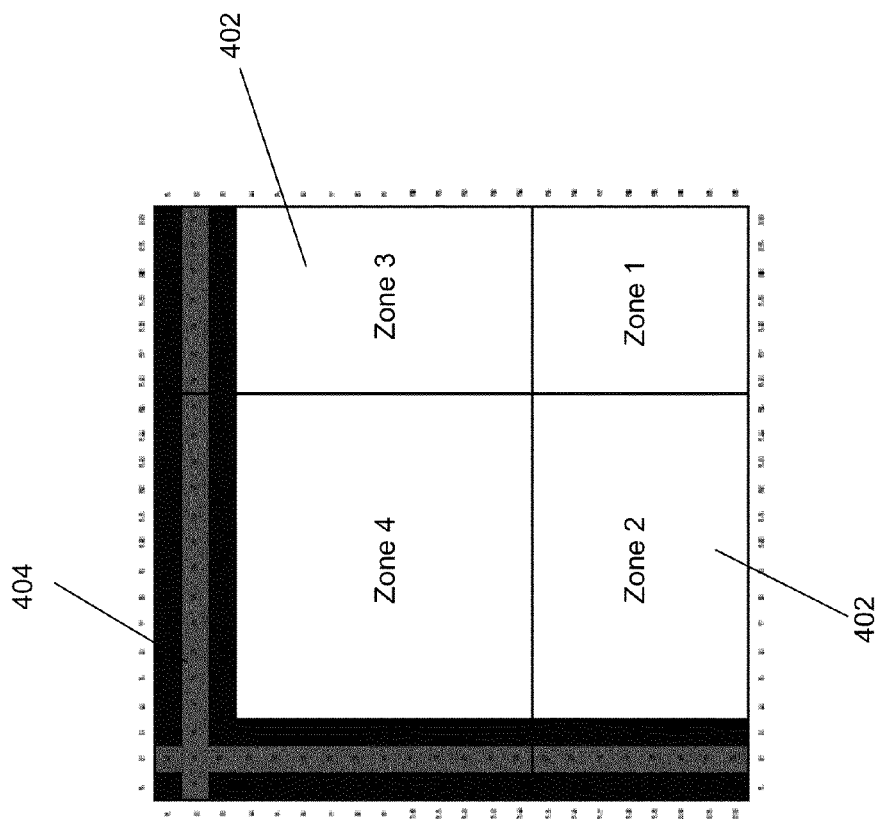
Figure 9A:
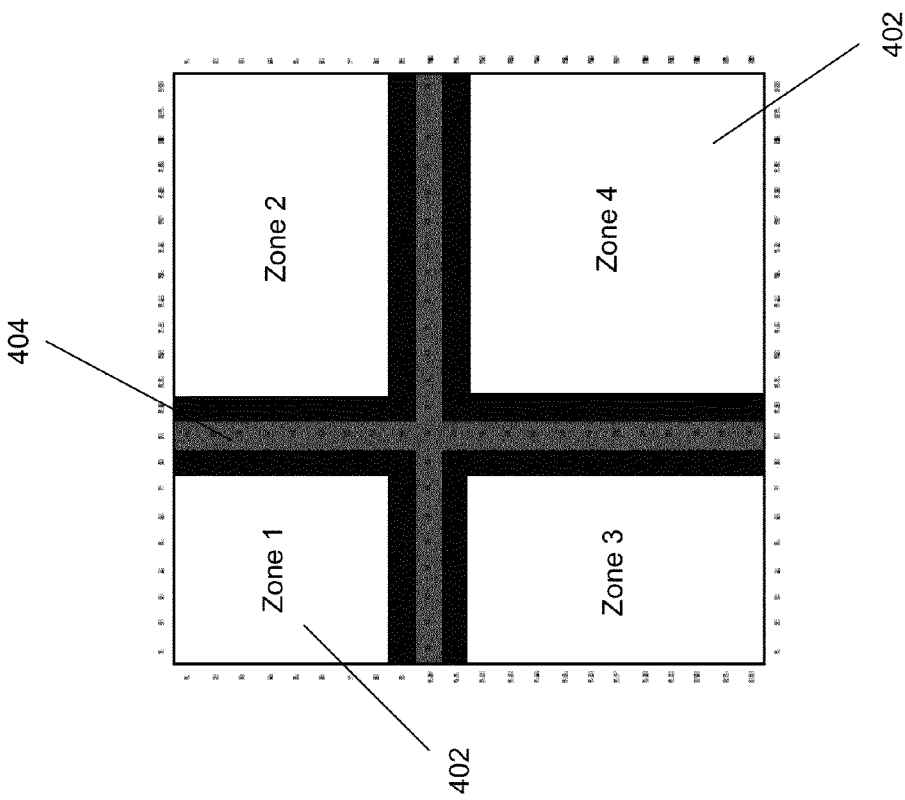
FIG. 9a shows a typical field of view of an image sensor relative to a cross feature.

Once the position of the cross 404 within the image is determined, the captured image can be manipulated to shift the cross feature into a corner, thereby recreating the fully encoded pattern within a single quadrant of the manipulated image. FIG. 9a shows a typical field of view of the sensor 112 relative to the cross 404. The portions of each pixel map 402 captured by the sensor are labeled as zones 1 to 4. FIG. 9b shows a virtual rearrangement of the image of FIG. 9a to place the cross 404 in one corner of the image and to reconstruct a full pixel map 402 in one quadrant.

In reality some overlapping of each of the zones will occur, dependant on the actual image sensor 112 used, the size of the field of view and the size of the encoded pattern. As the size of the encoded image 300 and field of view of the sensor 112 are well controlled, the microprocessor 202 is able to crop the image zones when rearranging the image.

Once the manipulated image is obtained, the pixel data can be interrogated to determine the encoded data. Use of the pixel maps 402 ensures that each pixel within the manipulated image is assigned to a particular data bit, dependant on its relative position to the cross 404. The pixel map 402 can also assign a weighting value to each pixel. Weighting values are used to apply increased significance to pixels contained within the body of a particular data bit than pixels at a data bit boundary. Due to the pixelation of the captured image there is a greater degree of confidence in the colour (black or white) of those pixels which are surrounded by other pixels within the same data bit than those which are adjacent another data bit.

FIG. 10 shows the position of each pixel and data bit in a pixel map 402. The position of each of the pixels comprising the data bits is represented by a number which is also the weighting value of that pixel. The weighted average intensity of each data bit can therefore be determined by the microprocessor 202. These weighted averages can be compared against threshold values to determine whether each data bit is black or white. Threshold values may be fixed, or may be based on intensity values of the captured image to automatically compensate for variations in image intensity. In this embodiment, a single parity bit is included to provide error checking. Alternatively, more data bits could be assigned to error checking to increase the robustness of the decoded data.

As previously mentioned, the device 100 may be able to deliver up to 80 doses, such that there are 81 positions, including a zero position, of the encoded member 406 relative to the housing 102. This number of positions can be encoded within 7 bits of data. As 7 bits could be used to encode up to 128 positions, a reduced coded set may be utilised, which maximises the number of white data bits.

Figure 11:
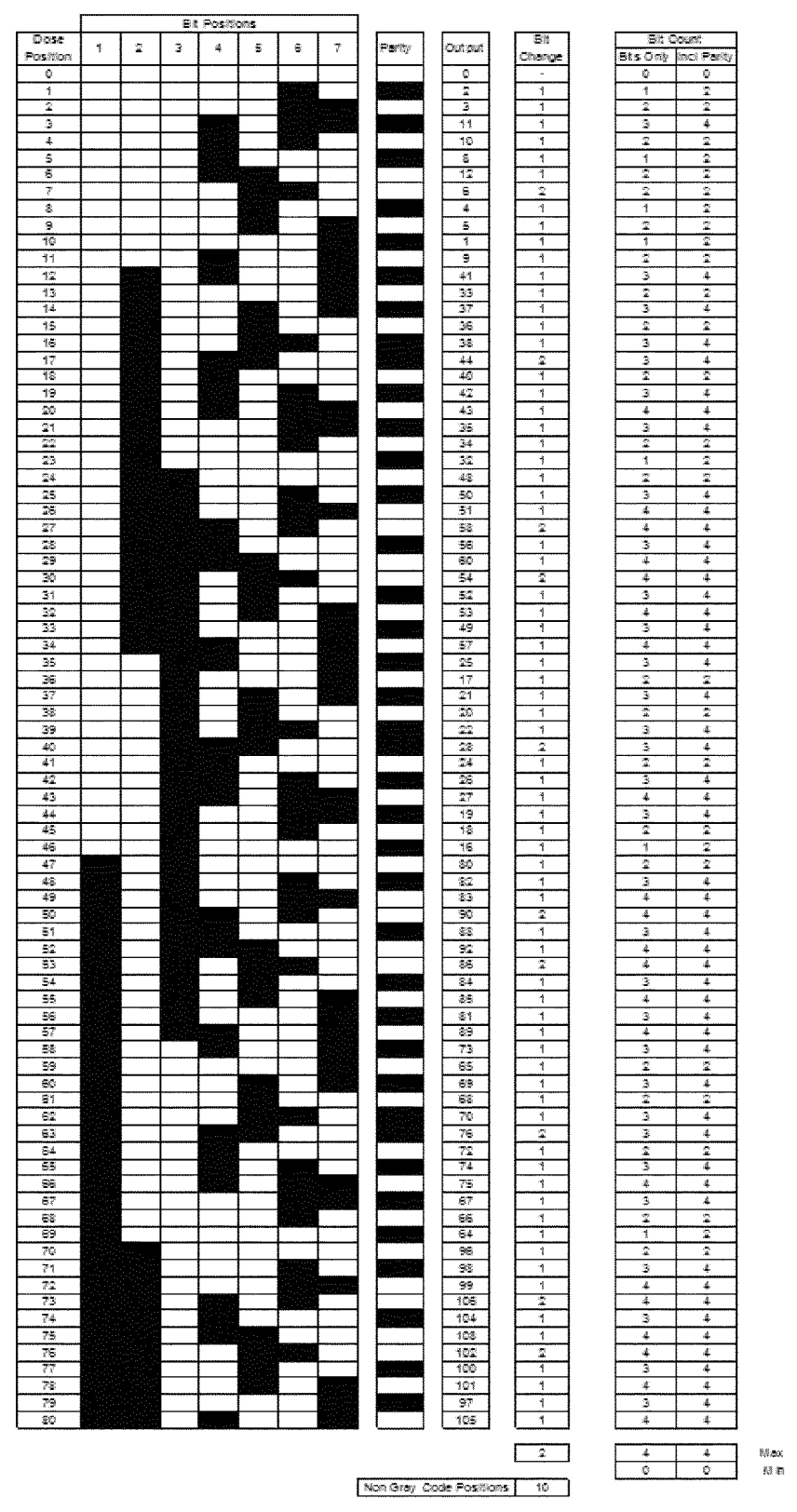
Figure 12:
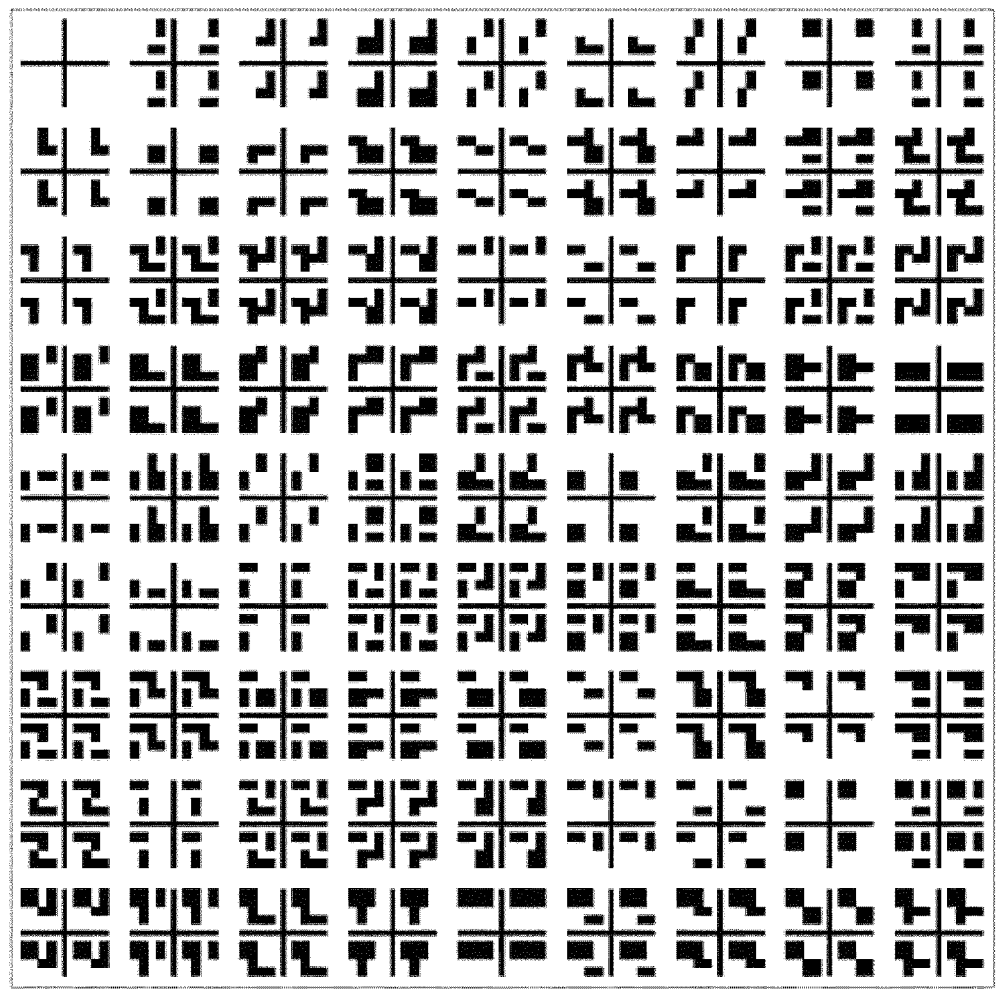
FIG. 12 shows 81 encoded images produced according to the table of FIG. 11.

The coded pattern shown in FIGS. 11 and 12 has a maximum of 4 black data bits across the 7 data bits and parity bit. Therefore at least 50% of the data bits are always white, maximising the image contrast between the cross 404 and the encoded data. This reduces the chance of an error in the detection of the position of the cross 404 within the captured image. FIG. 11 is a table illustrating the sense (high or low) of each bit for each of the 81 encoded positions for a "maximum white" code. FIG. 12 is a grid showing all 81 "maximum white" encoded images as they would be printed on to the track 110 of the encoded member 406.

Figure 13:
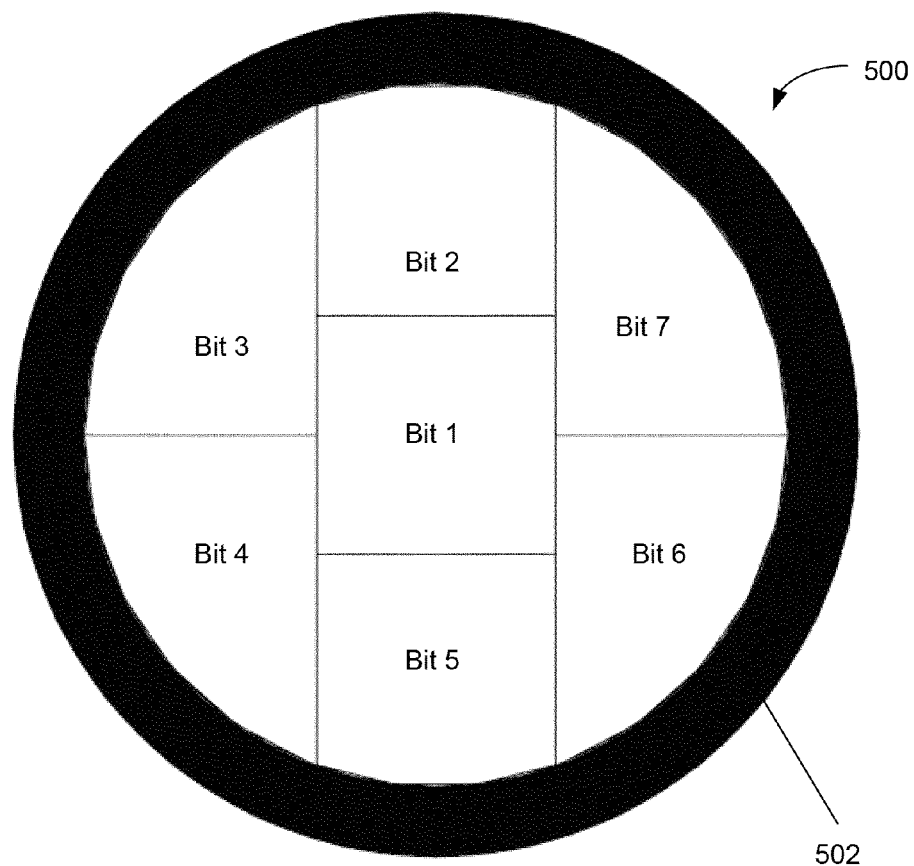
FIG. 13 shows a template for an encoded image.

Referring now to FIGS. 13 to 18, further embodiments of encoded images suitable for use in the present invention are shown. FIG. 13 shows a template 500 for an encoded image. The template 500 has a circular black band 502 as the geometric datum feature. The encoded data is contained within this circle 502, and consists of 7 binary data bits, numbered 1 to 7. The internal area of the circle 502 is therefore split into 7 segments and each segment is filled black to represent a "high" data bit, or white to represent a "low" data bit.

The field of view of the sensor 112 encompasses the whole of the encoded image and is arranged so as to capture an image containing the entire encoded image, including the circle 502. The position of the circle 502 within the captured image is determined by an algorithm, and hence the location of each of the data bits can be determined.

Figure 14:
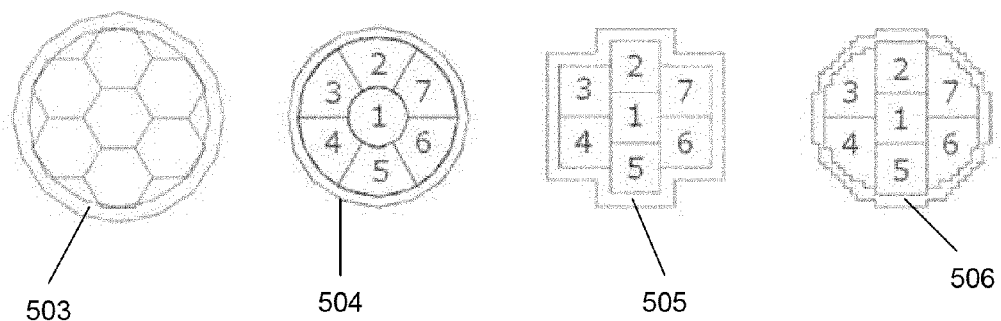
FIG. 14 shows some alternative encoded image templates.

FIG. 14 shows some possible alternative encoded image templates 503, 504, 505, 506 having a differently shaped outer boundary (datum feature) and/or differently shaped data segments. Any suitable geometric shape or feature could be used for the outer boundary and data segments.

Figure 15:
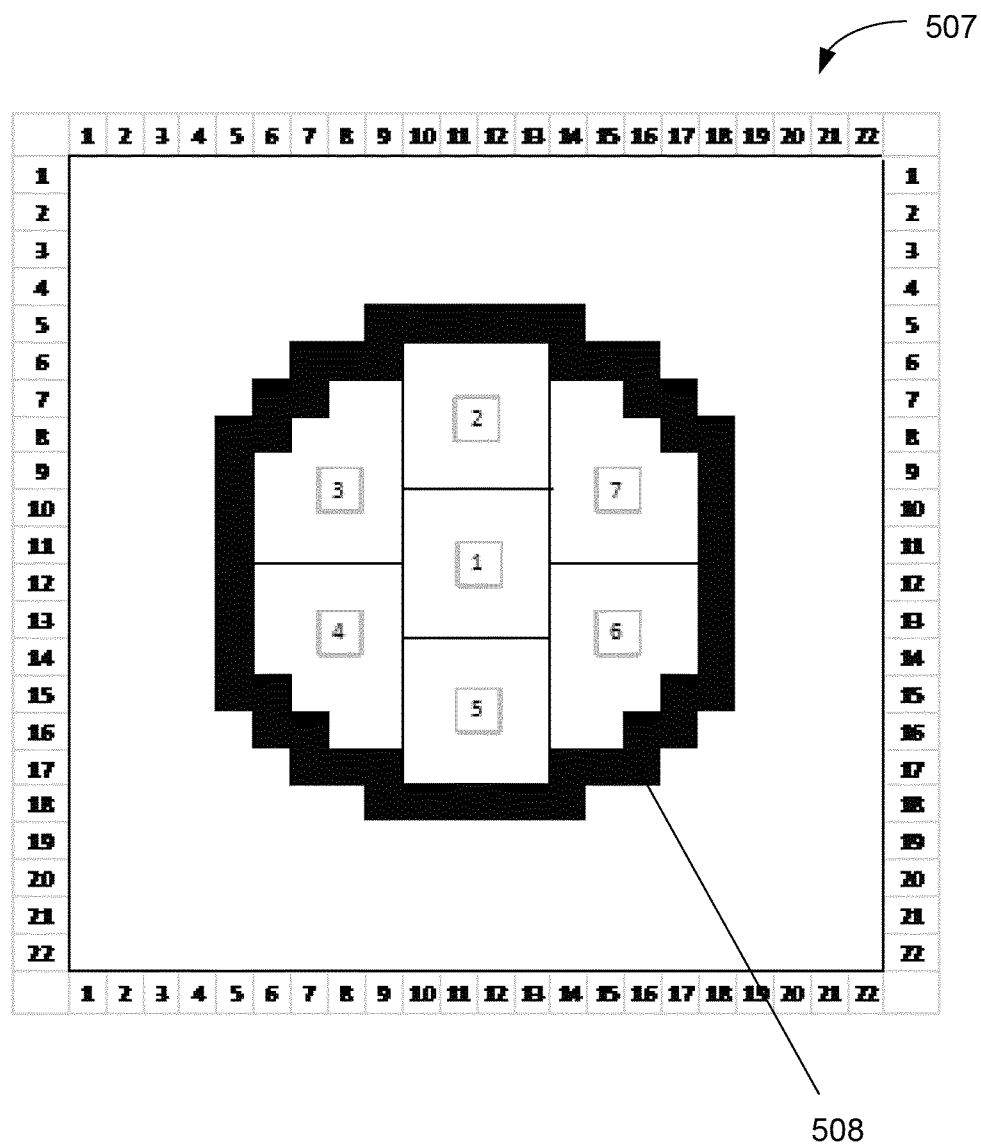
FIG. 15 shows a result of an image capture of the template of FIG. 13.

The sensor 112 captures a pixelated image in greyscale, with high intensity pixels representing white, and low intensity pixels representing black, areas of the pattern. FIG. 15 shows a result of this image capture. The captured image 507 comprises a pixelated circular feature 508. The image sensor 112 may have a pixel array of 22×22 pixels.

The microprocessor 202 then implements an algorithm to detect the position of the pixelated circular feature 508 within the image 507. The size of the circle 502 relative to the captured image 507 is known, as the pattern generation and image field of view are well controlled. The algorithm therefore searches the captured image 507 for a feature of a known shape and size. The output of the circle detection algorithm is a single pixel at the centre of the pixelated circle 508.

Prior to circle detection, an 3×3 edge detection spatial filter and a threshold filter are applied to the captured image, to generate a binary image with white pixels representing edges. The circle detection algorithm assumes that each detected edge pixel could be located on any part of the circumference of the pixelated circle 508, and therefore the centre of the circle could be offset from that edge pixel in any direction by a distance equal to the radius of the (printed) circle 502.

A virtual circle, of the same radius as the circle 502, is therefore created around each edge pixel. The virtual circle passes through a specific set of pixels in the detection array. Each time a virtual circle passes though a pixel in the detection array, a value associated with that pixel is incremented by 1. These virtual circles are generated for each edge pixel within the threshold filtered image. This routine generates a circle detection array containing an array of numbers. The array position with the highest number has the most virtual circles crossing it and therefore this array position corresponds to the captured image pixel which is the most likely solution for the centre of the pixelated circle 508.

The circle detection array extends beyond the field of view of the captured image, as an edge pixel at an edge or corner of the captured image would generate a virtual circle which extends up to 1 radius beyond the captured image. It is therefore possible to detect the position of a pixelated circle 508 the centre of which is outside of the field of view of the captured image.

Figure 16A:
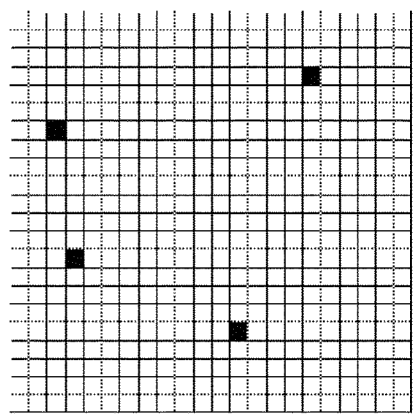
FIGS. 16a-f illustrate a basic example of a circle detection algorithm.
Figure 16B:
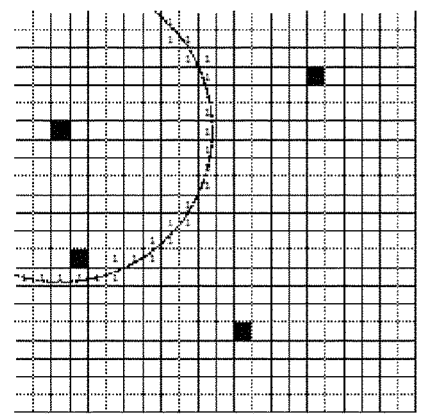
Figure 16C:
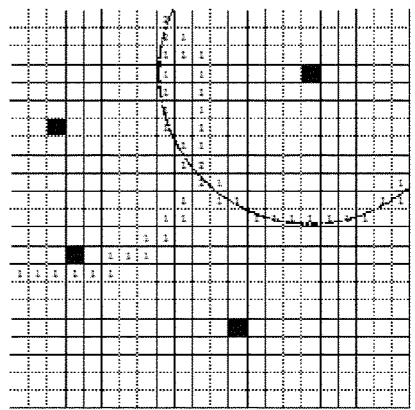
Figure 16D:
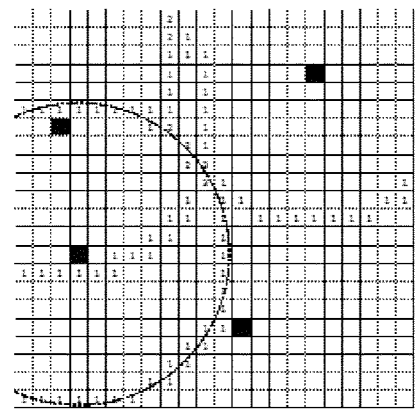
Figure 16E:
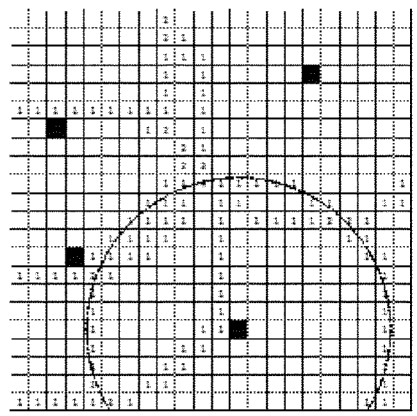
Figure 16F:
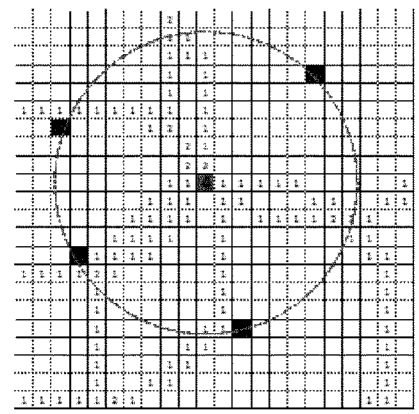

A basic example of the circle detection algorithm is illustrated in FIGS. 16*a-f*, using a simplified image with only four edge pixels. FIG. 16*a* shows the four detected edge pixels on a circle detection array. In FIG. 16*b* a first virtual circle is created around a first of the edge pixels. Each pixel of the circle detection array that this virtual circle passes through has a value associated with it incremented (from 0 to 1). This process is repeated in FIG. 16*c* for the second edge pixel, in FIG. 16*d* for the third edge pixel and in FIG. 16*e* for the fourth edge pixel. Once this process has been completed for all of the detected edge pixels, the microprocessor 202 searches the array to find the largest value associated with a pixel. In this instance, one pixel has a value of 4 and is determined to be the most likely centre of the circle, as shown in FIG. 16*f*.

Due to the pixelation of the encoded pattern and circle 502, it is possible that the centre of the circle will occur at a pixel vertex, rather than within a single pixel. In order to address this a 2×2 spatial filter is applied to the circle detection array to average the array value across four pixels. The highest value within the averaged circle detection array defines the most likely pixel vertex solution for the centre of the pixelated circle 508.

Threshold values and error checking can be applied within the algorithm to verify the results. Exemplary verification checks include:

The single pixel solution lies within the averaged pixel solution

Figure 17:
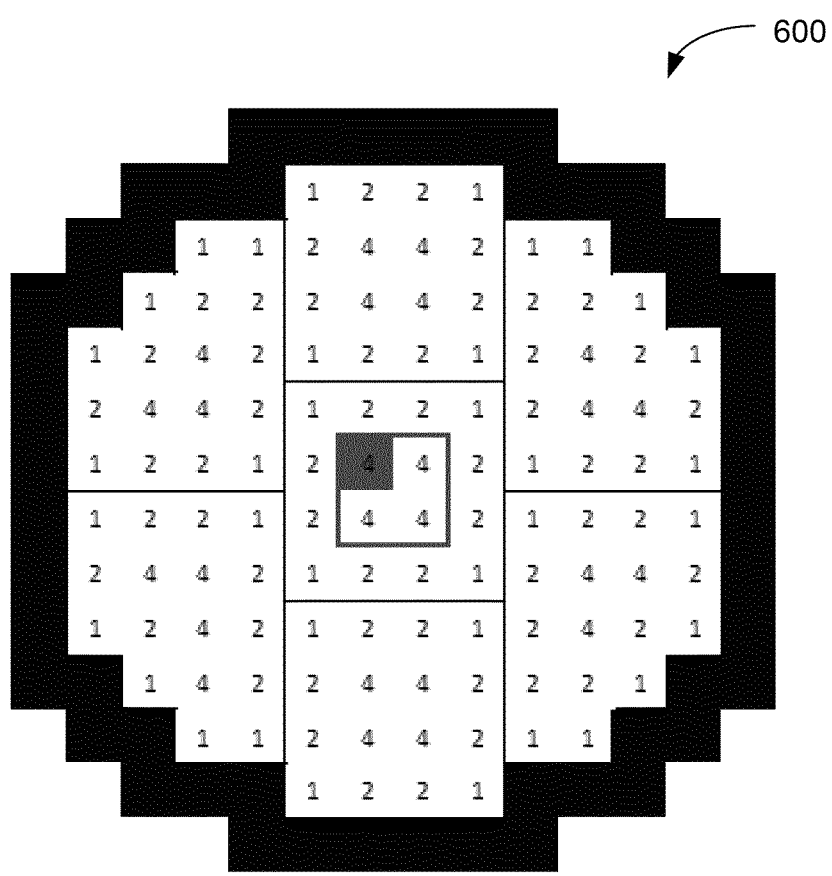
FIG. 17 shows the position of pixels in a pixel map.

The most likely solution is distinct from other possible solutions i.e. highest value in array/second highest value in array>confidence factor A sufficient number of valid edge pixels exist for the most likely solution i.e. highest value in array>threshold The centre pixel is within the captured image, such that all encoded data pixels are within the captured image Once the circle detection algorithm has identified and verified a pixel representing the centre of the pixelated circle 508, the captured image data can be interrogated to determine the status of each data bit. Referring to FIG. 17, a pixel map 600 assigns each pixel within the captured image to a particular data bit, dependant on its relative position to the central pixel. The pixel map can also assign a weighting value to each pixel. Weighting values are used to apply increased significance to pixels contained within the body of a particular data bit relative to those pixels at a data bit boundary. FIG. 17 shows a pixel map 600 in which each pixel is represented by a number which also indicates the weighting value given to that pixel.

The weighted average intensity of each data bit can therefore be determined by the microprocessor 202. These weighted averages can be compared against threshold values to determine whether each data bit is black or white. Threshold values may be fixed, or may be based on intensity values of the captured image to automatically compensate for variations in image intensity.

As with the previous embodiments, the 81 possible dose positions can be encoded within 7 bits of data. As 7 bits could encode up to 128 positions, a reduced coded set can be utilised. These reduced coded sets can assist in maintaining the distinction of the pixelated circle 508 relative to the encoded data within the circle.

Figure 18:
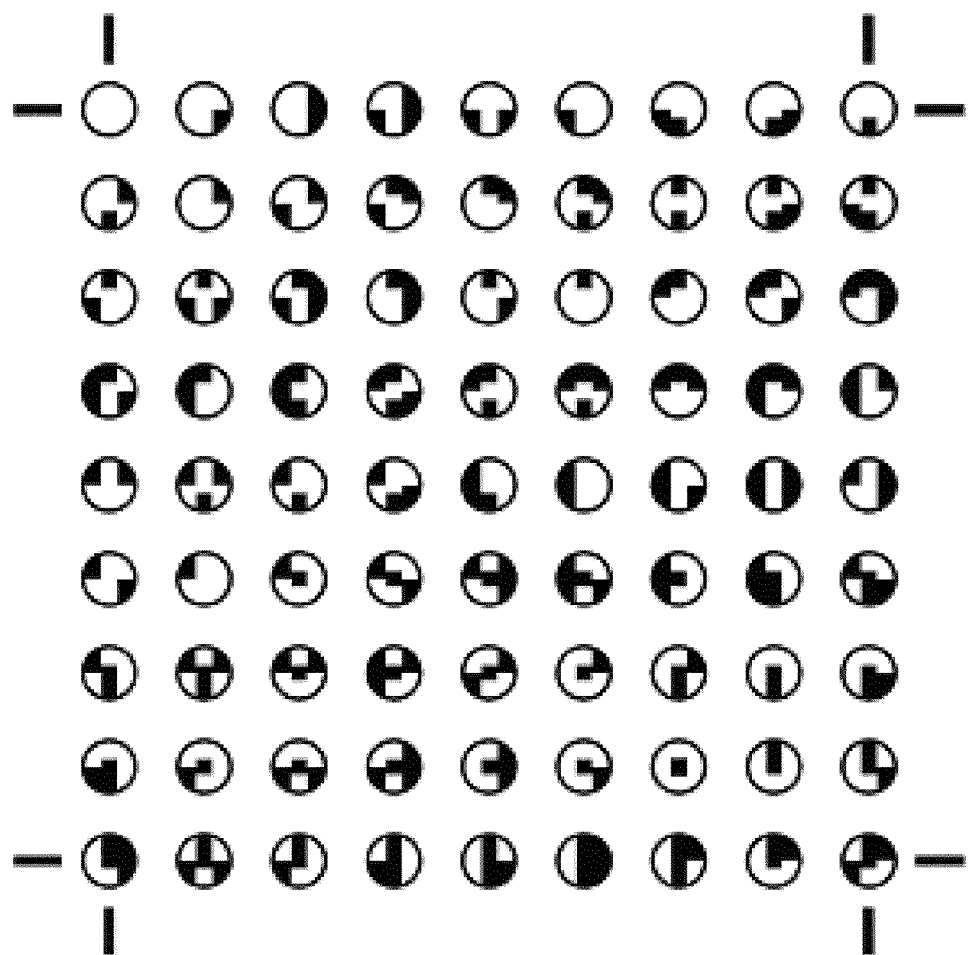
FIG. 18 shows 81 encoded images produced with the template of FIG. 13.

The coded pattern, shown in full in FIG. 18, has a maximum of 4 black data bits across the 7 data bits. Therefore at least 60% of the data bits are always white, maximising the image contrast between the circular feature 508 and the encoded data. Alternatively, a coded pattern may be used which maximizes the number of black data bits in the encoded image. Alternatively, a coded pattern could be used which maximizes either white or black and is a Gray code (in which only one bit changes sense between successive encoded images).

Once the status of each data bit is determined, and validated against threshold values, the rotational position of the encoded member 406 can be determined by comparing the coded output against a lookup table.

As well as determining the rotational position of the member 406, the microprocessor 202 may also determine whether the device 100 is in a dialling mode i.e. drug dose setting mode, or a drug delivery mode. The switch 216 may be any suitable micro-switch and may be coupled to both the microprocessor 202 and the dose button 416 supported by the rotatable dial 108. The state of the switch 216 may be changed when the dose button 416 is depressed and the microprocessor 202 may detect this change. An indication of the mode (dialling or delivery) of the device 100 may be displayed on the display 210.

When dispensing a selected dose, if for any reason the user does not dispense the full dose, the display 210 may be configured to show the dose which is remaining to be dispensed.

In some embodiments, the sensor 112 may be further configured to continuously measure the movement of the member 406 and to output relative translation data to the microprocessor 202. The microprocessor 202 is configured to determine a discrete number of units dialled and/or delivered from the received relative translation data. This allows incremental positional encoding of the member 406. To aid the sensor in distinguishing relative movement, the encoded member 406 may be provided with a particular surface finish such as shot-blasting or etching as well as a plurality of markings, such as printed dots. This relative translational detection may be provided in addition to the encoded images previously described and may act as a secondary positional check. In some alternative embodiments, successive images from the sensor 112 may be compared via a simple algorithm in order determine an offset between the images and therefore a rotational movement of the encoded member.

It will be appreciated that the above described embodiments are purely illustrative and are not limiting on the scope of the invention. Other variations and modifications will be apparent to persons skilled in the art upon reading the present application. For example, although the helical track 110 has been described as being applied to a member integral with the rotatable dose dial 108, the helical track 110 may instead be applied to any existing component of the drug dose setting mechanism 400 which moves rotationally, axially or both relative to the sensor 112 and which is, or can be made, visible to the sensor 112. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and c have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drug delivery device comprising;
a housing;
a cylindrical member configured to be rotatably supported inside the housing, wherein an outer surface of the cylindrical member is provided with a track comprising a sequence of encoded images, wherein the encoded images each encode a discrete rotational position of the cylindrical member, wherein each encoded image comprises an identical predetermined geometric feature, and wherein the predetermined geometric feature is a cross shaped feature that separates four adjacent identical code sections;
a sensor directed at the track of the cylindrical member and configured to capture an image of one or more of the encoded images; and
a processor configured to:
receive image data corresponding to the captured image from the sensor;
detect, using the received image data, a position of the predetermined geometric feature in the captured image;
based on the position of the predetermined geometric feature in the captured image, reconstruct a single code section from partial views of two or more of the identical code sections in the captured image; and
detect, using the received image data, encoded information at at least one position in the captured image that is predefined relative to the position of the predetermined geometric feature and offset from the position of the predetermined geometric feature.

2. A drug delivery device as claimed in claim 1, wherein the processor is configured to detect encoded information at plural locations in the image that are in different predefined positions relative to the geometric feature.

3. A drug delivery device as claimed in claim 2, wherein each predefined position relative to the geometric feature is defined by a pixel map comprising an arrangement of data bits.

4. A drug delivery device as claimed in claim 1, wherein each of the identical code sections comprises an arrangement of data bits.

5. A drug delivery device as claimed in claim 1, wherein the processor is configured to compare the received image data to a pixel map comprising an arrangement of data bits.

6. A drug delivery device as claimed in claim 3, wherein each data bit in the pixel map is comprised of a plurality of pixels and wherein each pixel of the pixel map has an associated weighting value determined by its position within its respective data bit.

7. A drug delivery device as claimed in claim 1, wherein the processor is configured:
to determine a discrete rotational position of the cylindrical member using the received image data;
to determine a selected drug dose using the discrete rotational position of the member; and
to cause the selected drug dose to be displayed on a display.

8. A drug delivery device as claimed in claim 1, wherein the processor is configured:
to determine a succession of discrete rotational positions of the cylindrical member using the received image data; and
to determine a direction of rotation of the cylindrical member using the succession of discrete rotational positions.

9. A drug delivery device comprising;
a housing;
a cylindrical member configured to be rotatably supported inside the housing, wherein an outer surface of the cylindrical member is provided with a track comprising a sequence of encoded images, wherein the encoded images each encode a discrete rotational position of the cylindrical member, and wherein each encoded image comprises an encoded pattern disposed within a boundary of an identical predetermined geometric feature;
a sensor directed at the track of the cylindrical member and configured to capture an image of one or more of the encoded images, wherein a field of view of the sensor is controlled such that the identical predetermined geometric feature has a known pixel size within the captured image; and
a processor configured to:

receive image data corresponding to the captured image from the sensor;

search the captured image for a pixelated feature having a shape of the predetermined geometric feature and the known pixel size;

detect, using the received image data, encoded information at at least one position in the captured image that is predefined relative to the position of the predetermined geometric feature and offset from the position of the predetermined geometric feature wherein each encoded image is disposed within a boundary of the geometric feature.

10. A drug delivery device as claimed in claim 9, wherein the processor is configured to compare the received image data to a pixel map comprising an arrangement of data bits and to determine which pixel represents a center of the predetermined geometric feature.

11. A drug delivery device as claimed in claim 9, wherein the predetermined geometric feature is a circular band.

\* \* \* \* \*